United States Patent [19]

Azam et al.

[11] Patent Number: 4,572,190

[45] Date of Patent: Feb. 25, 1986

[54] HYPERTHERMIA APPARATUS

[75] Inventors: Guy Azam, la Celle-Saint-Cloud; Guy Convert, Vincennes; Jacques Dufour, Orsay; Claude Jasmin; Joël Sidi, both of Paris, all of France

[73] Assignee: CGR/MEV, Buc, France

[21] Appl. No.: 612,368

[22] Filed: May 21, 1984

[30] Foreign Application Priority Data

May 26, 1983 [FR] France ............................. 83 08727

[51] Int. Cl.⁴ ........................................... A61N 1/40
[52] U.S. Cl. ................................ 128/399; 128/420 A; 128/804
[58] Field of Search ................ 128/399, 420 A, 422, 128/783, 804

[56] References Cited

U.S. PATENT DOCUMENTS

| 3,800,802 | 4/1974 | Berry | 128/422 |
|---|---|---|---|
| 4,095,602 | 6/1978 | Leveen | 128/420 A X |
| 4,148,321 | 4/1979 | Wyss et al. | 128/420 A |
| 4,346,715 | 8/1982 | Gammell | 128/422 |
| 4,397,313 | 8/1983 | Vaguine | 128/399 |
| 4,397,314 | 8/1983 | Vaguine | 128/399 |
| 4,448,198 | 5/1984 | Turner | 128/422 |

FOREIGN PATENT DOCUMENTS

| 1109280 | 6/1961 | Fed. Rep. of Germany ... 128/420 A |
|---|---|---|
| 818881 | 6/1937 | France . |
| 1083425 | 6/1954 | France . |
| 2252082 | 6/1975 | France . |
| 2365911 | 4/1978 | France . |

Primary Examiner—Anton O. Oechsle
Attorney, Agent, or Firm—Roland Plottel

[57] ABSTRACT

A hyperthermia apparatus primarily applicable to the treatment of tumors comprises at least three high-frequency generators connected to three electrodes. The electrodes are intended to be coupled to a patient's body which constitutes the load, thus producing a higher temperature rise in the vicinity of a fictitious electrode in the body. The generators have adjustable phases and amplitudes, the output of each generator being connected to each of the three electrodes.

7 Claims, 4 Drawing Figures

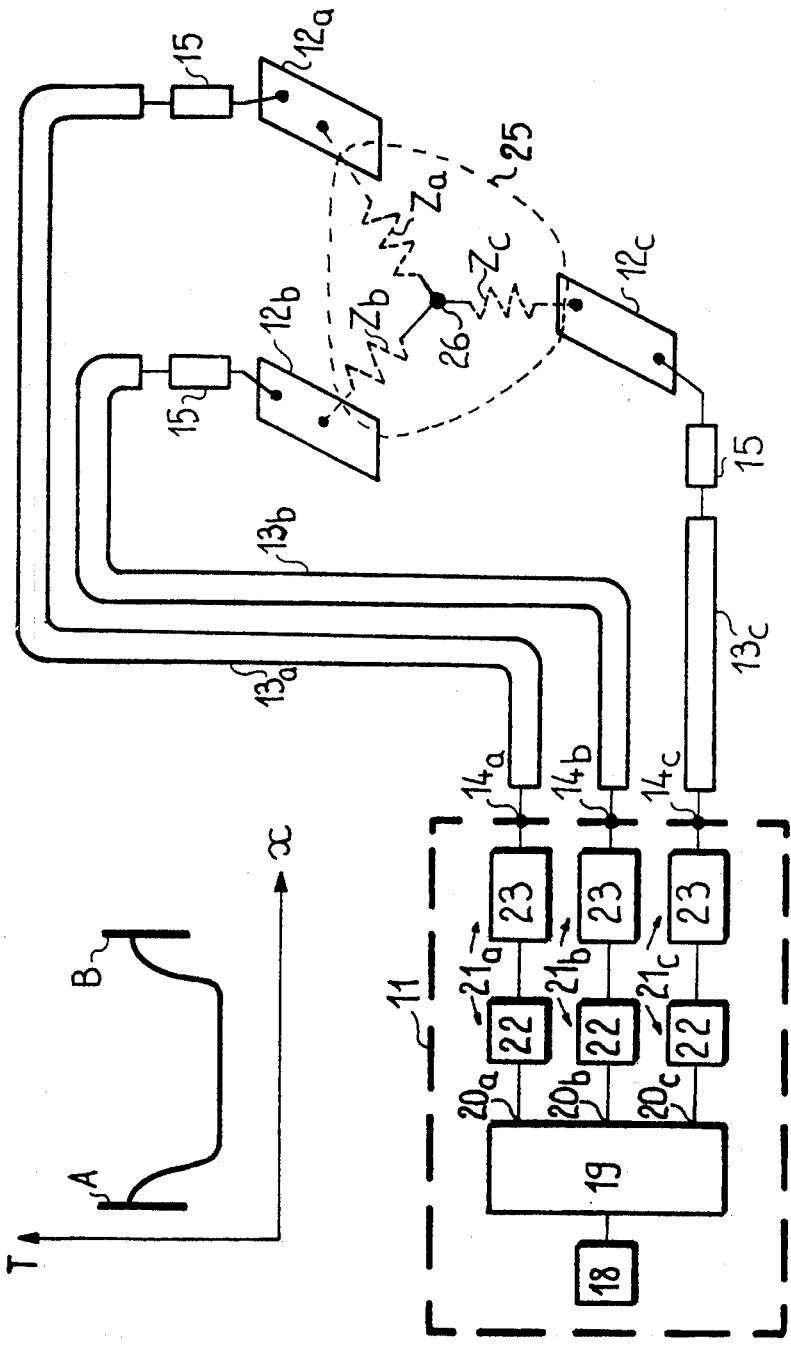

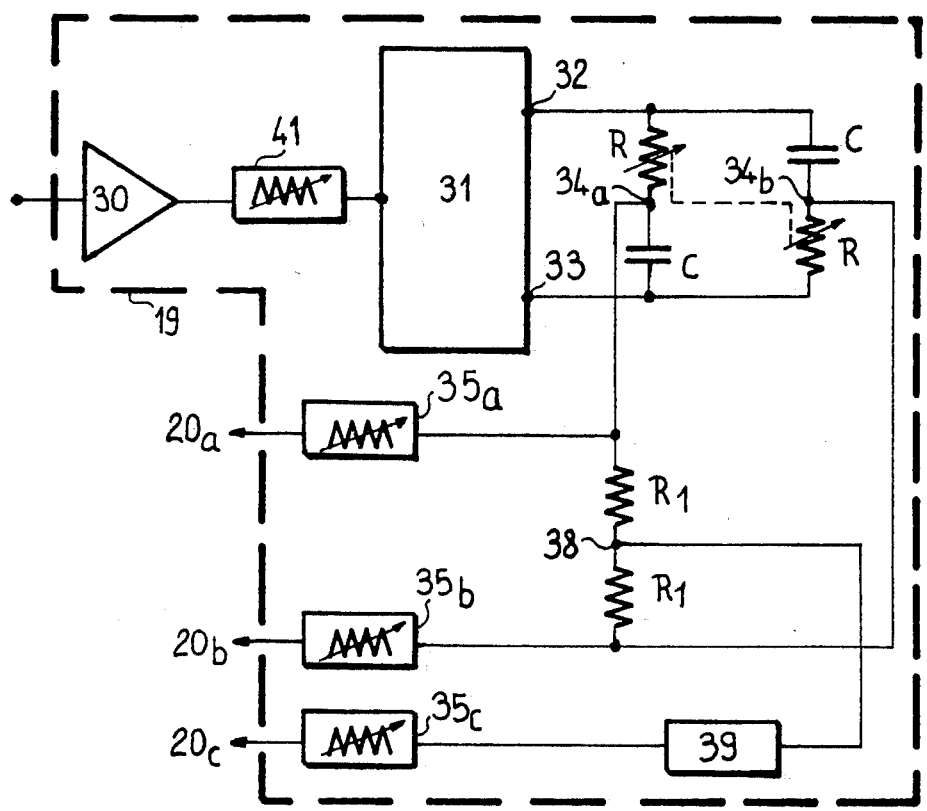
FIG_3
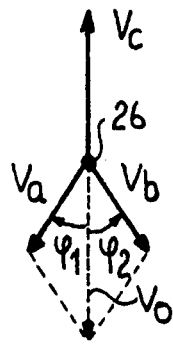
FIG_4

HYPERTHERMIA APPARATUS

BACKGROUND OF THE INVENTION

1. Field of the Invention

This invention relates to a hyperthermia apparatus or in other words a unit which generates high-frequency power for treating an affected area of a patient's body by producing a local elevation of temperature. The distinctive feature of the invention lies in the fact that it permits deep hyperthermia.

2. Description of the Prior Art

It is known that certain ailments can be treated by inducing a temperature rise of a few degrees in the affected region. For example, gonococcal infections can be treated in this manner since gonococci are totally destroyed at a temperature between 41° and 42°. This method is also very promising for the resorption of certain tumors, in particular by reason of the fact that they are irrigated to a lesser degree than adjacent healthy tissues and therefore less efficiently cooled, with the result that their temperature rises to higher levels than in healthy tissues when they are subjected to the action of microwaves.

In hyperthermia units of the type used experimentally up to the present time, two electrodes are placed on each side of the region to be heated (for example a dorsal electrode and a ventral electrode). These electrodes are connected to a high-frequency generator having a medium power rating (a few tens of watts) which operates at a frequency of the order of 1 MHz or 10 MHz. In order to comply with current standards, a frequency of 13.56 MHz is often adopted.

However, a system of this type is subject to serious drawbacks since the distribution of high-frequency energy dissipated within the volume delimited by the two electrodes is not uniform. The curve of distribution between the two electrodes has substantially the shape of a bowl. In other words, a higher temperature rise is observed in the immediate vicinity of the two electrodes, the temperature-rise ratio between the adjacent zones of the electrodes and the center of the interelectrode space being of the order of 2 to 3. This is attended by two disadvantages. In the first place, the effectiveness of the treatment is reduced when the affected region is located at an appreciable depth. Secondly, there is a potential danger of burning in areas close to the skin. An attempt has been made to solve this problem by interposing between the electrodes and the patient a predetermined volume of water trapped within a flexible envelope provided with an inlet and an outlet so as to permit circulation and therefore surface cooling. Under these conditions, the temperature distribution curve exhibits a falloff in the vicinity of the electrodes but this produces only a slight improvement in deep treatment. It is in fact hardly possible to increase the high-frequency power since cooling remains effective to a depth corresponding to only the first few millimeters of tissue for reasons of thermal conductivity.

SUMMARY OF THE INVENTION

The invention overcomes these disadvantages by utilizing a number of electrodes which is greater than two and providing the possibility of phase adjustment between the electrodes. The general result thereby achieved is the same as if a polyphase high-frequency system of this type generated a fictitious electrode (or a virtual ground) within the patient's body which constitutes the load, the temperature rise being greater in the vicinity of the fictitious electrode.

In more precise terms, the invention therefore relates to a hyperthermia apparatus comprising high-frequency generating means and electrodes designed to be coupled to a patient's body which constitutes the load. The distinctive feature of the invention lies in the fact that said generating means comprise at least three generators having adjustable phases and amplitudes and that the output of each generator is connected to one electrode aforesaid.

By means of a system comprising four or five electrodes (or more), the number of phase and amplitude adjustments makes it possible to localize the hot zone with precision, to shape the hot zone and to adjust its temperature at will. However, the very number of available adjustments calls for experience and skilful operation by the user. It is for this reason that, in certain applications and in particular the treatment of the abdominal and pelvic regions, it may prove advantageous to reduce the number of electrodes to the minimum number required for the application of the invention (that is to say three electrodes) and to couple certain adjustments in order to make the apparatus easier to operate. The three-electrode arrangement is in fact fairly well suited to coupling to the abdominal region by placing one pair of electrodes at the rear (buttocks electrodes) and the third electrode in front (pubic electrode).

Provision is also made for an arrangement which consists in interposing bags (not shown in the drawings) or flexible-walled containers filled with water between each electrode and the patient's body in order to ensure more effective surface cooling but also in order to achieve better electrical matching between the generator and the load.

BRIEF DESCRIPTION OF THE DRAWINGS

Other features of the invention will be more apparent upon consideration of the following description of a three-electrode hyperthermia apparatus, reference being made to the accompanying drawings, wherein :

FIG. 1 is a graph illustrating the spatial distribution of the temperature rise between two hyperthermia electrodes in accordance with the technique of the prior art ;

FIG. 2 is a block diagram of a three-electrode hyperthermia apparatus in accordance with the invention ;

FIG. 3 is a block diagram of a phase-shifting circuit for use in the apparatus of FIG. 2 ;

FIG. 4 is a vector diagram illustrating the composition of the phase-shifted signals and the creation of the fictitious electrode.

DESCRIPTION OF THE PREFERRED EMBODIMENT

FIG. 1 shows the spatial distribution of dissipated power between two electrodes A, B of a conventional hyperthermia system. The abscissa x designates the direction which passes substantially through the center of the electrodes at right angles to these latter and the ordinate T designates the temperature rise. It is observed that this temperature rise is distinctly higher in the vicinity of the electrodes. The disadvantages of this situation have been developed in the foregoing. The basic concept of the invention consists in arranging a polyphase and at least three-phase system connected to at least three electrodes in order to generate a fictitious electrode located within the volume delimited by the real electrodes. Under these conditions, when the real electrodes exchange high-frequency energy between them, it is just as if the same number of pairs of electrodes were provided and one of these latter (namely the fictitious electrode which is common to all the pairs) were located at the center of the patient's body. Thus several zones of the patient's body are heated in several preferential directions (facing the electrodes) between the fictitious electrode representing a ground and each of the electrodes. It is thus apparent that, in respect of each preferential direction, the temperature rise distribution has the shape illustrated in FIG. 1. In consequence, the temperature rise in the vicinity of the fictitious electrode is relatively substantial since it results from the contributions of all the hyperthermia systems constituted by the pairs of electrodes which include said fictitious electrode each time.

FIG. 2 illustrates the essential means of a system in accordance with the invention and comprising high-frequency three-phase generating means 11 having adjustable phases and amplitudes, three corresponding electrodes 12a, 12b, 12c which are intended to be coupled to the patient's body and three cables 13a, 13b, 13c forming a quarter-wave transmission line and connected respectively between three outputs 14a, 14b, 14c of the generating means and said electrodes. Small variable inductors 15 are inserted in series between the electrodes and the transmission lines in order to compensate for the differences in length of the connections to these latter.

The generating means 11 comprise a high-frequency oscillator 18, a phase-shifting and attenuating circuit 19 which will be described below and has three outputs 20a, 20b, 20c for phase-shifted high-frequency signals having adjustable phases and amplitudes, and three amplifier chains 21a, 21b, 21c connected respectively between the outputs 20 and the outputs 14. In accordance with the example, each amplifier chain is a cascade assembly consisting of a first high-frequency amplifier 22 of relatively low power (50 watts maximum) and of a second high-frequency amplifier 23 having a higher power rating (1 kW at a maximum). Depending on requirements, provision could be made for a single amplifier or on the contrary for more than two amplifiers. When the electrodes are coupled to a patient's body 25 which constitutes the load, the situation is exactly the same as if a star network of three impedances Za, Zb, Zc were enclosed within the tissues and were to generate a fictitious electrode 26 within the patient's body. The position of this fictitious electrode depends on the ratios of phases and amplitudes of the signals applied to the electrodes. For the reasons mentioned earlier, the tissues in the vicinity of the fictitious electrode are subjected to more intense heating than in the remainder of the interelectrode space.

FIG. 3 shows a possible embodiment of the circuit 19. This circuit is more particularly designed to generate the signals to be applied to one pair of electrodes (for example the electrodes 12a, 12b) which perform the function of buttocks electrodes and on the other hand to the third electrode 12c which performs the function of pubic electrode. The phase shifts between the pair of electrodes and the third electrode comply with a characteristic law which will hereinafter become apparent and is particularly advantageous for treatment of the abdominal region. The phase-shifting and attenuating circuit 19 comprises a preamplifier 30 which receives on its input the high-frequency signal of the oscillator 18 and a first phase-inverter 31, the input of which is connected to the output of the preamplifier and which has two outputs 32, 33 for delivering signals in opposite phase. The design concept of an inverter of this type is conventional and within the capacity of any one versed in the art. The outputs 32, 33 are coupled to the terminals of two antiparallel-connected resistance-capacitance circuits. Both the resistors R and the capacitors C of the two circuits have the same value. The two resistors R are variable and coupled but the capacitors C could also be variable. The connection nodes 34a, 34b between resistor and capacitor of the two R-C circuits are connected respectively to the amplifier chains 21a, 21b via respective adjustable attenuators 35a, 35b. The phase-shifted signals derived from the R-C circuits are therefore those which will be applied to the pair of electrodes 12a, 12b after amplification. Furthermore, a series connection of two impedances R1 having the same value is connected between the nodes 34a, 34b. The common node 38 of these two impedances is connected to the input of a second phase inverter 39. The output of this inverter is connected to the amplifier chain 21c via an adjustable attenuator 35c. A variable attenuator 41 for general power regulation is inserted, for example, between the preamplifier 30 and the phase inverter 31.

It is apparent from FIG. 4 that, with an arrangement of this type, the phases of the signals applied to the pair of buttocks electrodes are always symmetrical ($\rho_1 = \rho_2$) with respect to a phase origin which is the origin of the signal available at the node 38. In consequence, the signals applied to the third electrode are always in phase opposition with respect to said phase origin. In other words, the voltage vector Vc of the third electrode is always in opposition to the vector Vo resulting from the geometrical summation of the two voltage vectors Va, Vb of the pair of buttocks electrodes whilst the vector Vo has a zero phase shift with respect to the phase origin. Postulating that the attenuators 35 all have the same adjustment, the position of the fictitious electrode 26 within the patient's body can be displaced towards the pubic electrode 12c when the absolute value of the phase $|\rho_1| = |-\rho_2|$ decreases since the voltage vector Vc of the electrode 12c depends on the composition of the voltage vectors Va, Vb. Furthermore, by producing action on the attenuators 35, the fictitious electrode 26 can be displaced on each side of the direction at right angles to the pubic electrode 12c if necessary in order to reach the zone to be treated by producing an unbalance of the system. This makes it possible to place the corresponding heating zone at any desired location within the interelectrode space.

What is claimed is:

1. A hyperthermia apparatus comprising high-frequency generating means and electrodes designed to be coupled to a patient's body for treatment of abdominal and pelvic regions which constitutes the load, wherein said generating means comprises a high frequency oscillator, a phase-shifting circuit and at least three generators having adjustable phases and amplitudes and wherein the output of each generator is connected to a corresponding electrode, and in which provision is made for three electrodes consisting respectively of a pair of electrodes or buttocks electrodes and of a third electrode or pubic electrode, wherein said phase-shifting circuit comprises means for maintaining the phases of the signals applied to said pair of electrodes substantially symmetrical with respect to a phase origin and means for maintaining the phase of the signal applied to the third electrode substantially in opposition to said phase origin.

2. An apparatus according to claim 1, wherein said phase-shifting circuit comprises:
- a first phase inverter which is connected so as to receive signals derived from said oscillator at its input and which delivers signals in phase opposition at two outputs;
- two oppositely connected resistance-capacitance circuits in which the two resistors or the two capacitors are variable and coupled, said circuits being connected between the two outputs of said first phase inverter;

and wherein the connection node between resistance and capacitance of each resistance-capacitance circuit is connected to an amplifier or an amplifier chain which supplies one of the electrodes of said pair.

3. An apparatus according to claim 2, wherein an adjustable attenuator is inserted between each connection node aforesaid and the corresponding amplifier or amplifier chain.

4. An apparatus according to claim 2 wherein a series connection of two impedances is connected between the two aforesaid connection nodes and wherein the common node of said two impedances is connected to the input of a second phase inverter whose output is connected to an amplifier or an amplifier chain which supplies said third electrode.

5. An apparatus according to claim 4, wherein an adjustable attenuator is inserted between the output of said second phase inverter and the corresponding amplifier or amplifier chain.

6. An apparatus according to claim 3, wherein a series connection of two impedances is connected between the two aforesaid connection nodes and wherein the common node of said two impedances is connected to the input of a second phase inverter whose output is connected to an amplifier or an amplifier chain which supplies said third electrode.

7. An apparatus according to claim 6, wherein an adjustable attenuator is inserted between the output of said second phase inverter and the corresponding amplifier or amplifier chain.

* * * * *